United States Patent [19]

Annis

[11] Patent Number: 5,493,596
[45] Date of Patent: Feb. 20, 1996

[54] HIGH-ENERGY X-RAY INSPECTION SYSTEM

[76] Inventor: Martin Annis, 65 Banks St., Cambridge, Mass. 02138

[21] Appl. No.: 486,035

[22] Filed: Jul. 7, 1995

Related U.S. Application Data

[63] Continuation of Ser. No. 291,338, Aug. 17, 1994, abandoned, which is a continuation of Ser. No. 147,388, Nov. 3, 1993, abandoned.

[51] Int. Cl.⁶ ................................................. G01N 23/201
[52] U.S. Cl. ................................................ 378/57; 378/146
[58] Field of Search ................................. 378/145, 146, 378/147, 151, 4, 57, 106, 101

[56] References Cited

U.S. PATENT DOCUMENTS

| | | | |
|---|---|---|---|
| Re. 28,544 | 9/1975 | Stein et al. | 378/146 |
| 4,430,568 | 2/1984 | Yoshida et al. | 378/57 |
| 4,503,332 | 3/1985 | Annis | 378/146 |
| 4,745,631 | 5/1988 | Paolini | 378/146 |
| 4,769,829 | 9/1988 | Webb et al. | 378/146 |
| 4,839,913 | 6/1989 | Annis et al. | 378/44 |
| 4,879,734 | 11/1989 | Schreckendgust et al. | 378/57 |
| 4,995,066 | 2/1991 | Harding et al. | 378/146 |
| 5,038,370 | 8/1991 | Harding et al. | 378/146 |
| 5,091,924 | 2/1992 | Bermbach et al. | 378/57 |
| 5,179,581 | 1/1993 | Annis | 378/57 |
| 5,224,144 | 6/1993 | Annis | 378/146 |

*Primary Examiner*—David P. Porta
*Assistant Examiner*—Don Wong
*Attorney, Agent, or Firm*—Cesari and McKenna

[57] ABSTRACT

A high-energy X-ray inspection system comprises an X-ray source for generating high energy X rays for inspecting the contents of large objects. The source is contained within an enclosure having an integrally-formed precollimator device that limits the radiation emitted from the source to form a "fan-beam" of X rays. A novel rotating cylindrical collimator converts the fan-beam into a pencil-beam of X rays, which is further limited by a fixed-slit collimator. The high-energy pencil-beam penetrates the entire area of an object and is intercepted by a detector, which transforms the X rays into image data for presentation on a display screen.

8 Claims, 4 Drawing Sheets

HIGH-ENERGY X-RAY INSPECTION SYSTEM

This is a continuation of application Ser. No. 08/291,338, filed 08/17/94, now abandoned; which is a continuation of application Ser. No. 08/147,388, filed on Nov. 3, 1993, now abandoned.

FIELD OF THE INVENTION

This invention relates generally to X-ray inspection systems and, more specifically, to high-energy, "pencil-beam" X-ray systems for inspecting the contents of cargo containers en route during sea, land or air transportation.

BACKGROUND OF THE INVENTION

Bulk transport using sea cargo containers is a traditional means for shipping freight, dating as far back as the 1860s. The reasons for bulked, rather than packaged, transport are clearly economic since bulk handling requires much less labor for loading and unloading the ships that carry the cargo. Cargo container shipping has become even more popular with the establishment of standard container sizes, e.g., 20 or 40 feet long, 8 feet high and 8 feet wide. This has led to use of cargo containers on major routes throughout the world, including the development of shipping networks where main ports, whether sea, land or air, act as distribution centers.

However, the use of cargo containers has made it difficult for authorities to inspect incoming/outgoing commerce. Because of their widespread use and the lack of effective content inspection, cargo containers are often used to transport contraband, including weapons, explosives, drugs and valuables. Accordingly, there is a need to provide systems that can effectively inspect the contents of these containers; X-ray systems may be used for this purpose.

The most common X-ray system used to produce images for cargo inspections is a "line-of-detectors" system 10, as depicted in FIG. 1. This system comprises a source 12 for generating a beam of X rays and a fixed-slit collimator 14 that limits the beam to a thin sheet or "fan-beam". A high-voltage linear accelerator is used as the X-ray source to emit radiation having a peak energy of 6 to 15 million electron-volts (MeV). X-ray image data are acquired by a plurality of detectors, i.e., the line-of-detectors 16, which are arranged to intercept the fan-beam after the beam exits the inspected object 18. Typically, there are 500 to 1000 detectors arrayed along a vertical axis. Two-dimensional images are obtained by moving the object horizontally, past the detector array. The high-energy X-rays used in this system may penetrate an object that is approximately three times thicker than that detectable by another X-ray surveillance system, namely a pencil-beam system.

This latter known system 20, illustrated in FIG. 2, is used to inspect large objects 22, such as empty tractor-truck trailers. A conventional, low-energy X-ray source 24 is located at the center of a rotating wheel collimator 25 having a plurality of apertures 26 disposed therein. The source comprises a conventional X-ray tube that emits a cone of X rays having a peak energy of 450 thousand electron-volts (KeV). As the collimator rotates about the source, the cone of X rays is collimated into a pencil-beam by the rotating apertures. A fixed crossslit collimator may be situated between the collimator 25 and the object 22 to further define the pencil-beam in one dimension. A line of X rays is then formed that sweeps across and through the object. A single X-radiation detector 28 intercepts the X rays as they exit the object. The position of the pencil beam is measured at the rotating wheel to determine a line of the X-ray image. As in the line-of-detectors system, the remaining portions of the image are acquired as the object moves past the detector.

Pencil-beam systems are less expensive than the line-of-detectors system mainly because the pencil-beam system requires only one detector. In addition, the line-of-detectors system utilizes solid state diodes to detect light photons produced in scintillating materials of the detectors. These diodes have a higher intrinsic noise level than the photomultipliers used in pencil-beam system detectors. Moreover, the pencil-beam system requires little shielding because of its low, instantaneous X-ray flux due to the small cross-sectional area of the beam. The pencil-beam system can also efficiently produce an X-ray "back-scatter" image that facilitates identification of contraband material hidden in the walls of the cargo containers.

Unlike the line-of-detectors system, a conventional pencil-beam system cannot use a conventional linear accelerator as the X-ray source because the accelerator emits X rays in short bursts, followed by periods of quiescence, which are too long to allow image formation. The pencil-beam system requires numerous, i.e., 500 to 1000, samples during each sweep of the X-ray beam to acquire sufficient picture elements (pixels) to resolve an image. The latency between X-ray bursts generated by the linear accelerator compels a slow rotation of the collimator, thereby resulting in an unacceptably long inspection time for objects. Accordingly, conventional pencil-beam systems are forced to use lower-energy X-ray sources which emit X rays continuously and which cannot penetrate cargo containers. The present invention is directed to providing an improved pencil-beam system that can inspect those containers fast and efficiently.

SUMMARY OF THE INVENTION

Briefly, an X-ray inspection system constructed in accordance with the invention comprises, *inter alia*, a high-energy X-ray source and a novel rotating cylindrical collimator for generating intense pencil-beams of X-rays used to produce image data of the contents of large and dense objects, such as cargo containers.

The high-energy source is a pulsed linear accelerator that generates a cone of X-rays from high-energy electron pulses having a repetition rate of approximately 10,000 pulses per second. The accelerator has a generally long rectangular shape and may be provided with an enclosure having an integrally-formed precollimator. The precollimator enclosure comprises shielding with a slit that is centered in the direction of the X-ray cone and which converts the cone into a "fanbeam" of X rays prior to its interception by the rotating collimator.

The prior art rotating wheel collimator is not suitable for use in a pencil-beam system using this type of linear accelerator because a very large diameter wheel would be needed to clear the length of the accelerator. In addition, the wheel rim must be approximately 2 feet thick and constructed of lead or steel. Accordingly, the design of a bearing system to support such a large, and heavy, wheel is impractical.

Therefore, the novel rotating collimator is provided as a cylinder with a helical slit extending near its outer surface. The fan-beam enters the rotating collimator through the helical slit on a slanting chord of the collimator and exits the collimator through that chord. As the fan-beam enters the helical slit, the cylindrical collimator rotates to form a pencil-beam that sweeps across the object, from its top to bottom.

A fixed-slit collimator may be situated between the rotating collimator and the object to further limit the cross-section of the pencil-beam in one dimension. The limited pencil-beam is directed through the object, where it is intercepted by a detector as the object moves in a direction transverse to the direction and plane of the beam, thereby providing image data of the entire contents of the object.

The detector comprises a plurality of scintillating screens optically coupled to a plurality of photo-multipliers. When the X rays of the limited pencil-beam strike the scintillating screens, visible light is produced and detected by the photo-multipliers which, in turn, generate data signals used to form an image. In accordance with an aspect of the invention, those photo-multipliers not in the vicinity of the incident X rays are de-activated, thereby reducing "after-glow" noise and improving the quality of the image data.

An advantage of the novel inspection system is that the system generates high-energy, pencil-beam X rays that can penetrate objects significantly thicker, e.g., by approximately 50%, than those penetrable by previous inspection systems. That is, these high-energy pencil-beams may penetrate thicknesses on the order of 19 inches of steel. Previous systems can only penetrate 10–12 inches of steel.

Moreover, the novel inspection system is capable of generating these high-energy pencil-beams at a faster rate than conventional systems, thereby enabling fast and efficient scanning operations of large containers. For example, the pulse repetition rate for X-ray bursts generated by a conventional linear accelerator is less than 1000 pulses per second. Since pencil-beam systems typically sample at least 500 times during each sweep of the beam, the fastest time that a conventional linear accelerator could accomplish a single sweep is 0.5 seconds. To inspect a 40-foot long container, 4000 discrete sweeps are required, resulting in an inspection time for the entire container of more than 2000 seconds or approximately 33 minutes. In contrast, the novel inspection system can execute a single sweep of the beam, while sampling 500 times, in 0.05 seconds, thereby inspecting the same container in approximately 3 minutes.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
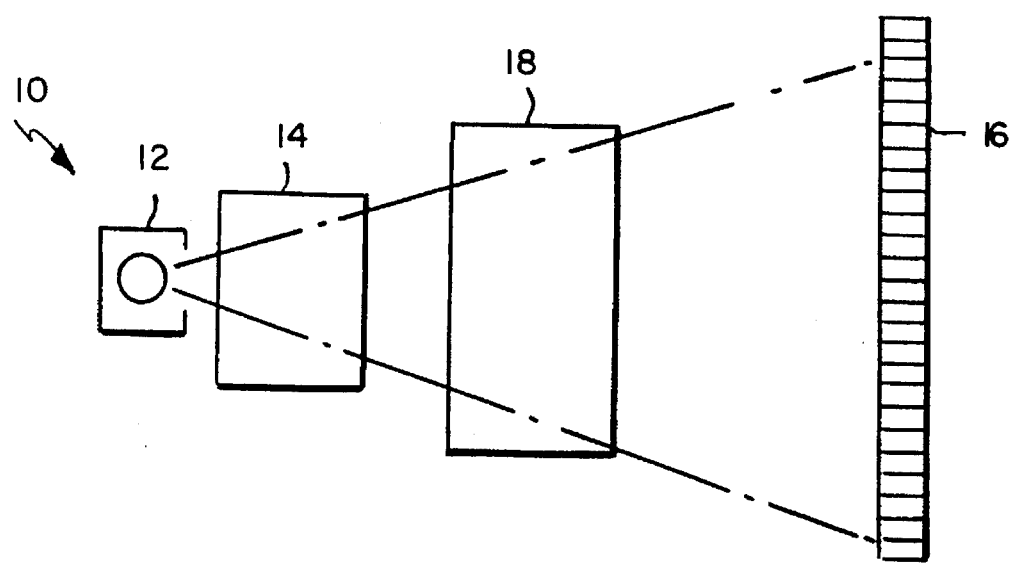
FIG. 1 is a side view of a prior art, line-of-detectors X-ray system.
Figure 2:
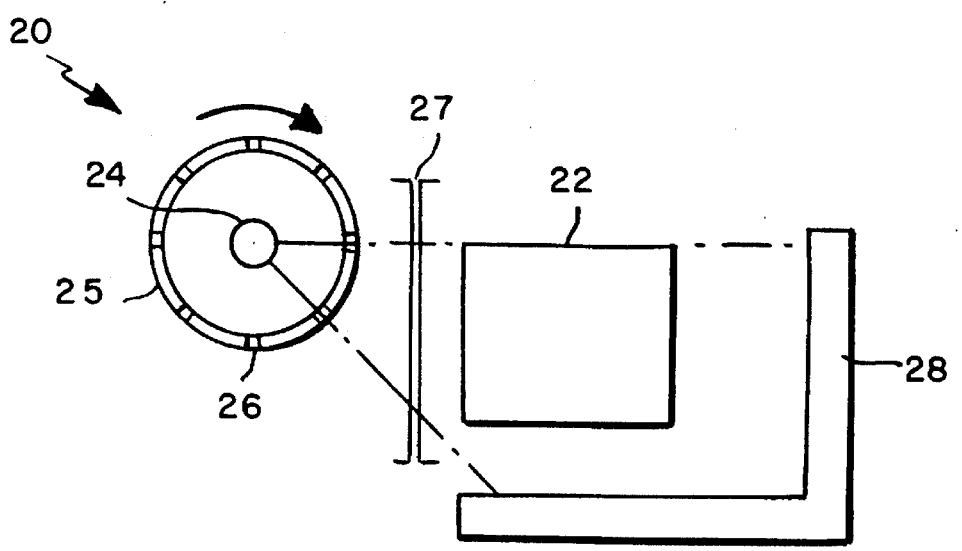
FIG. 2 is a side view of a prior art, pencil-beam X-ray system.
Figure 3:
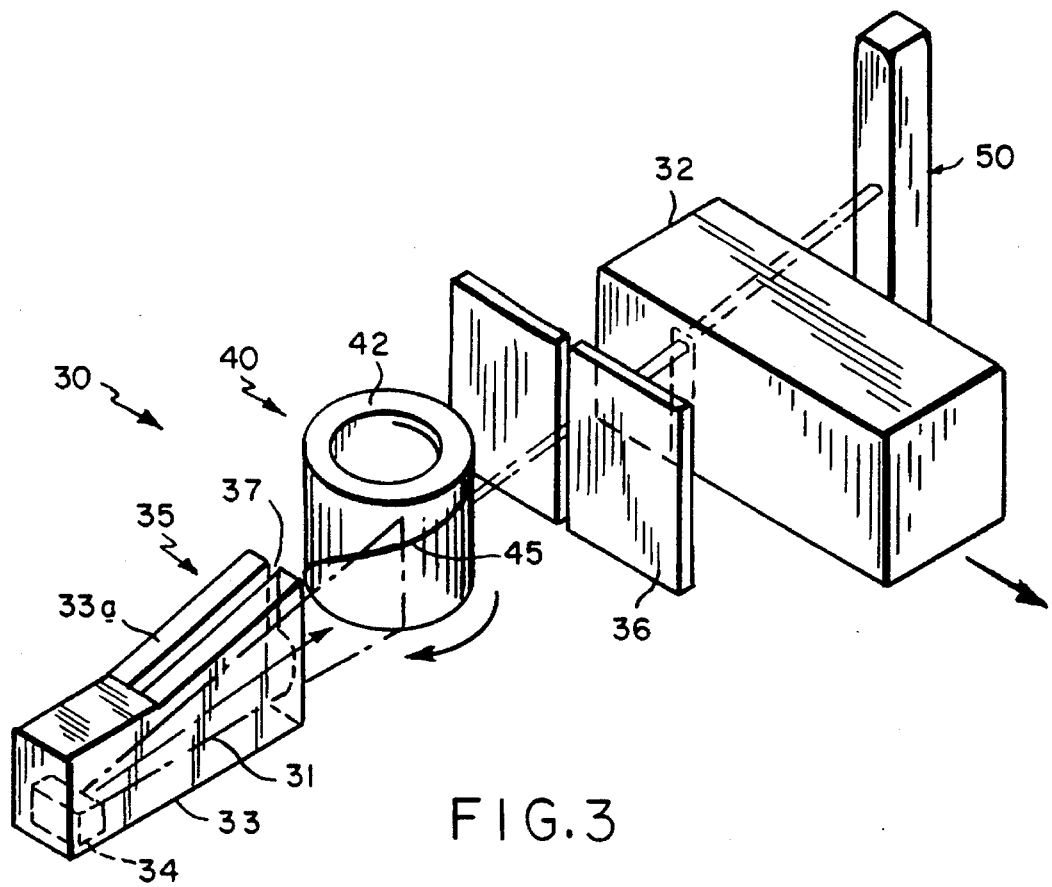
FIG. 3 is an isometric view of a high-energy, X-ray inspection system in accordance with the invention.
Figure 3A:
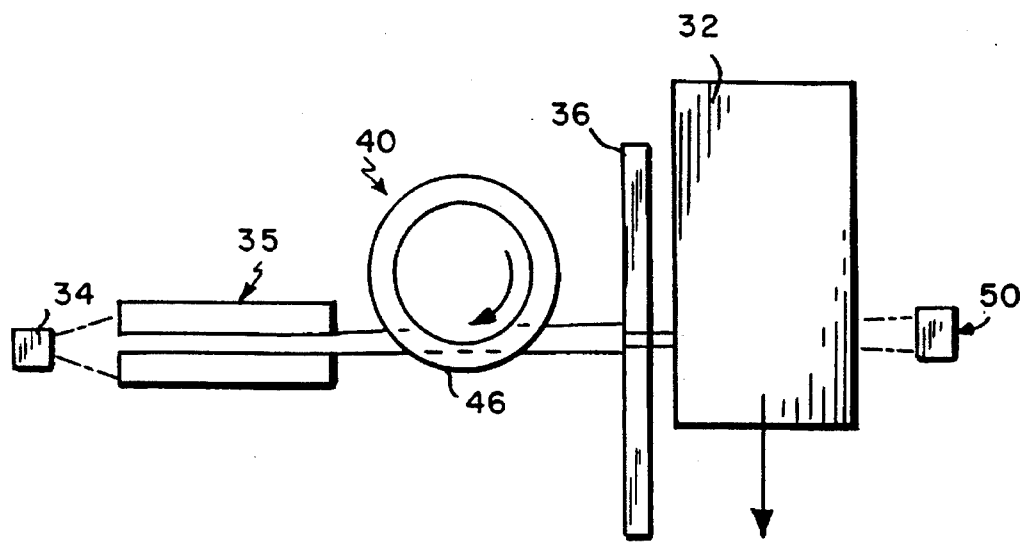
FIG. 3A is a plan view of the high-energy, X-ray inspection system shown in FIG. 3.

FIGS. 3 and 3A depict the high-energy X-ray inspection system 30 in accordance with the invention. The elements of the system are not drawn to scale for purposes of ease of depiction and ease of description, although the figures depict their relationship relative to one another. The system 30 is typically used for inspecting the contents of large objects 32, such as cargo containers; however, these systems may be employed for other industrial applications, such as for inspecting rockets and large hole castings.

A typical cargo container has a rigid steel frame with rigid corner posts and steel infill panels. As noted, these containers typically measure 20 or 40 feet in length by 8 feet in height by 8 feet in width. The maximum loaded container weighs approximately 20 tons (20-foot containers) or 40 tons (40-foot containers).

Referring to FIG. 3, the inspection system 30 comprises a high-energy X-ray source 34 for generating high-energy X rays that radiate as a cone. The source is contained within an enclosure 33 having an integrally-formed precollimator device 35 that limits the radiated cone along its center axis 31 to form a "fan-beam" of X rays. A novel rotating cylindrical collimator 40 converts the fan-beam into a pencil-beam of X rays, which is further limited by a fixed-slit collimator 36. The high-energy pencil-beam penetrates the entire area of an object and is intercepted by a detector 50, which transforms the X rays into image data for presentation on a display screen (not shown).

The high-energy X-ray source 34 is preferably a linear accelerator having an X-ray pulse repetition rate of about 10,000 pulses per second (pps). The accelerator emits a cone of X rays with a peak energy of 6 to 11 MeV and an X-ray flux of approximately 3000 Roentgens per minute at a distance of one meter on the center axis 31 of the cone. Preferably, the source radiates a 40° cone, i.e., 20° on either side of the center axis 31, which determines the height of the rotating collimator 40 and its distance between the source and object.

Specifically, the accelerator generates pulses of high-energy electrons that penetrate a target, e.g., a sheet of tungsten 2 mm thick, to produce pulses of X-ray beams. The pulsed beams preferably have a duration of 1 microsecond and are separated from each other by approximately 0.1 millisecond. A linear accelerator suitable for use as the high-energy X-ray source is a "Mini-Linatron" 6–9–11 MeV linear accelerator manufactured by Varian Inc. of 3045 Hanover Street, Palo Alto, Calif. 94304-1129. When utilized in the system of the invention, these X rays may penetrate up to 19 inches of steel, which represents a 50% increase in penetration over prior inspection systems.

Because the linear accelerator is a pulsed source of X rays, each X-ray pulse emitted from the accelerator may be measured by a reference X-ray detector (not shown) positioned near the X-ray beam leaving the linear accelerator. A corresponding signal frown the detector is processed with the reference detector signal to generate an output pulse having a ratio of the two signals. This effectively compensates for any variations in the output of the accelerator.

The precollimator 35 comprises a large shield 33a with a stationary slit 37 that filters all the radiation emitted by the source except for a preliminary fan-beam of X rays. The stationary shield 33a is typically composed of lead. To efficiently shield a source of radiation, the shield 33a should be close to the source; accordingly, the precollimator 35 is integrally-formed within the enclosure 33 containing the accelerator. In the illustrative embodiment, the enclosure is approximately 4 feet wide, 3 feet high and 8 feet long and, including the source, may weigh between 5 and 10 tons.

The slit 37 is centered along the center axis 31 of the X-ray cone and directs the resulting fan-beam towards the rotating cylindrical collimator 40 and then onto the object 50. To enhance the spacial resolution of an image of the object, the fan-beam should be as thin as possible; however, the beam should be dimensioned to retain sufficient flux to form the image. Therefore, the width of the beam is preferably 1 centimeter as it emerges from the slit 37.

Figure 4:
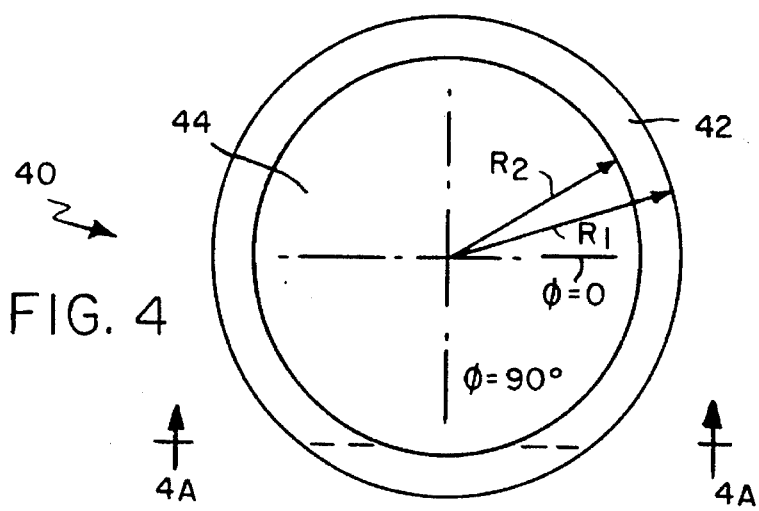
FIG. 4 is a plan view of a rotating cylindrical collimator in accordance with the invention.

In accordance with the invention, the novel rotating cylindrical collimator 40 converts the fan-beam into a plurality of pencil-beams that form a sweeping line. Referring to FIG. 4, the collimator 40 is a cylinder with an outer shell 42 and an inner cavity 44. In the illustrative embodiment, the radius $R_1$ measures 2 feet to the outer surface of the shell 42 and the radius $R_2$ is 1.59 feet to its inner surface. Accordingly, the outer shell is preferably 5 inches thick and, preferably, it is constructed of solid steel. A conventional motor and bearing "on-axis" arrangement (not shown) rotates the collimator at a rate of 10 revolutions per second or 600 revolutions per minute.

Referring again to FIG. 3, a helical slit 45 extends along the outer surface of the collimator 40. Specifically, the slit 45 is defined by a straight line from the source that penetrates the outer shell 42 and proceeds down its outer surface as the collimator rotates, thus forming a helix around the circumference of the collimator 40. In the illustrative embodiment of the invention, the collimator stands 6 feet high and, although the length of the helical slit 45 is slightly less, it is sufficiently long to receive the 40° cone emitted from the source. Preferably, the helical slit 45 is offset a small, predetermined length, e.g., 4 inches, from both the top and bottom of the collimator. Because the collimator is made of steel, these lengths hold the collimator together and simplifies its manufacture.

As the collimator rotates about its center axis, the orientation of the slit changes and the pencil-beams exiting the collimator are constantly displaced in a downward, sweeping direction to form a line of beams. In the illustrative embodiment, each beam exiting the collimator has an area of 0.5 centimeters by 0.5 centimeters.

Specifically, during each full rotation of the collimator 40, the exiting pencil-beam sweeps from the top of the object 32 to its bottom in approximately 0.1 seconds. The angle of rotation of the rotating collimator determines the height of these beams impinging the object. Each line of an image may be established by measuring this angle. By moving the object transversely through the beam, lines of data may be recorded to form a two-dimensional, X-ray transmission image of the object.

Figure 4A:
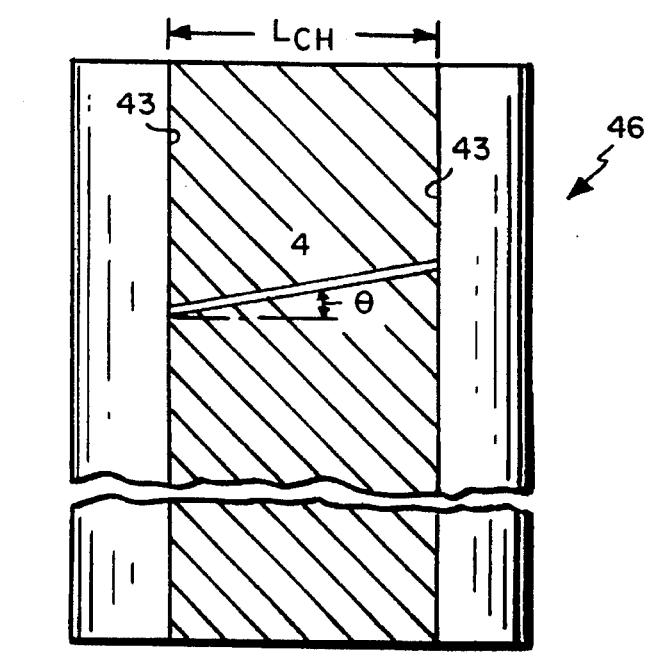
FIG. 4A is a sectional view along line 4A,4A of a chord of the rotating cylindrical collimator of FIG. 4.

Referring now to FIG. 3A, the fan-beam enters the rotating collimator 40 through the helical slit 45 on a chord 46 of the outer shell 42 and exits the collimator through that cord. This is more clearly seen in FIG. 4A, which depicts a cross-section of the chord 46 along the lines 4A,4A (FIG. 4) of the collimator. Here, the helical slit 45 is shown as having a uniform width that is oriented at an angle Θ which changes as the collimator turns. The fan-beam of X rays exiting the precollimator 35 consists of a plurality of pencil-beams oriented at various angles in a plane generally transverse to the slit 45. Of these angular pencil-beams, only the one that is oriented at the angle Θ is allowed to pass through the slit 45.

The position of the slit 45, i.e., tangent to the inner surface 43 of the collimator, provides a long path length for attenuating random X rays. That is, the length of the cord, $L_{CH}$, is preferably 2.41 feet, which is sufficient to effectively absorb the X rays that are not passed through the slit 45.

Figure 4B:
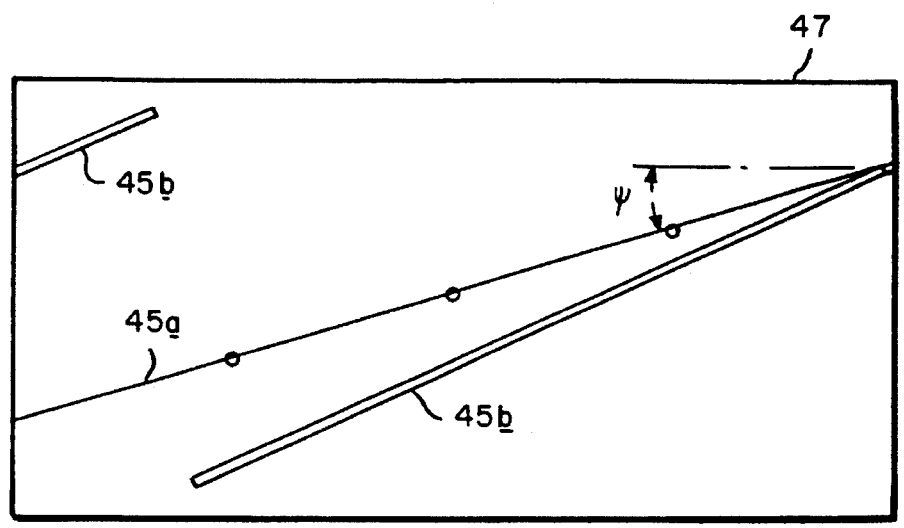
FIG. 4B depicts a "development" of the outer surface of the rotating cylindrical collimator.

As the collimator rotates, the slit 45 moves nearly horizontally, as illustrated in the "development", i.e., unrolling, of the outer surface 47 of the collimator 40 in FIG. 4B. The single line 45a shows the entry of the pencil-beam through the helical slit 45 and the double lines 45b show its exit. The initial slit angle ψ is preferably 16° to minimize "fuzziness" of the exiting beam.

Refer also to FIG. 4. Since the angle of rotation of the collimator, i.e., angle φ, is independent of the angle of the pencil-beam in the plane of the collimator, i.e., angle Θ, the velocity of the pencil-beam may be adjusted by altering the angle Θ by changing the location of the slit at discrete points along the shell 42. This enables, e.g., the beam to linger at the bottom and top of the sweeping line of pencil-beams in order to compensate for the decrease in radiation intensity at the edge of the fan-beam. This decrease is characteristic of all linear accelerators and conventional X-ray sources. In addition, the width of the slit 45 may be varied at discrete points along the helical slit 45 to also alter the radiation intensity at corresponding points along the sweeping line of beams.

Refer again to FIG. 3. Situated between the rotating collimator 40 and the object 32 is a fixed-slit collimator 36 configured to further limit the pencil-beam along the direction of the beam. The fixed-slit collimator 36 is preferably arranged close to the inspected object 32 to ensure that the beam is small along the transverse axis as it impinges the object, thereby improving the resolution of the image. Accordingly, the size of the beam as it impinges the object is preferably less than 1 centimeter by 1 centimeter.

As noted, cargo containers are generally standard in size, e.g., 8 feet by 8 feet by various lengths. In the illustrative embodiment, the rotating cylindrical collimator 40 generates an 8 foot vertical sweep of pencil-beams across the front portion of the container 32 every 0.1 seconds. The container is then moved 0.5 centimeters and another 8-foot sweep is generated. A conventional conveyer system (not shown) moves the object transversely through the pencil-beam of X rays. Preferably, the cargo container moves 40 feet in 200 seconds and the entire container can be scanned in 3.33 minutes.

Figure 5:
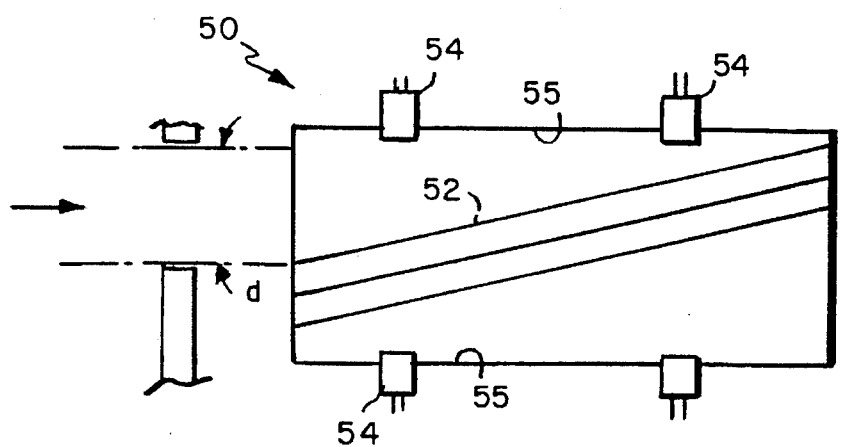
FIG. 5 is a plan view of a detector, including scintillating screens and photo-multipliers, for use in the high-energy X-ray inspection system of the invention.
Figure 5A:
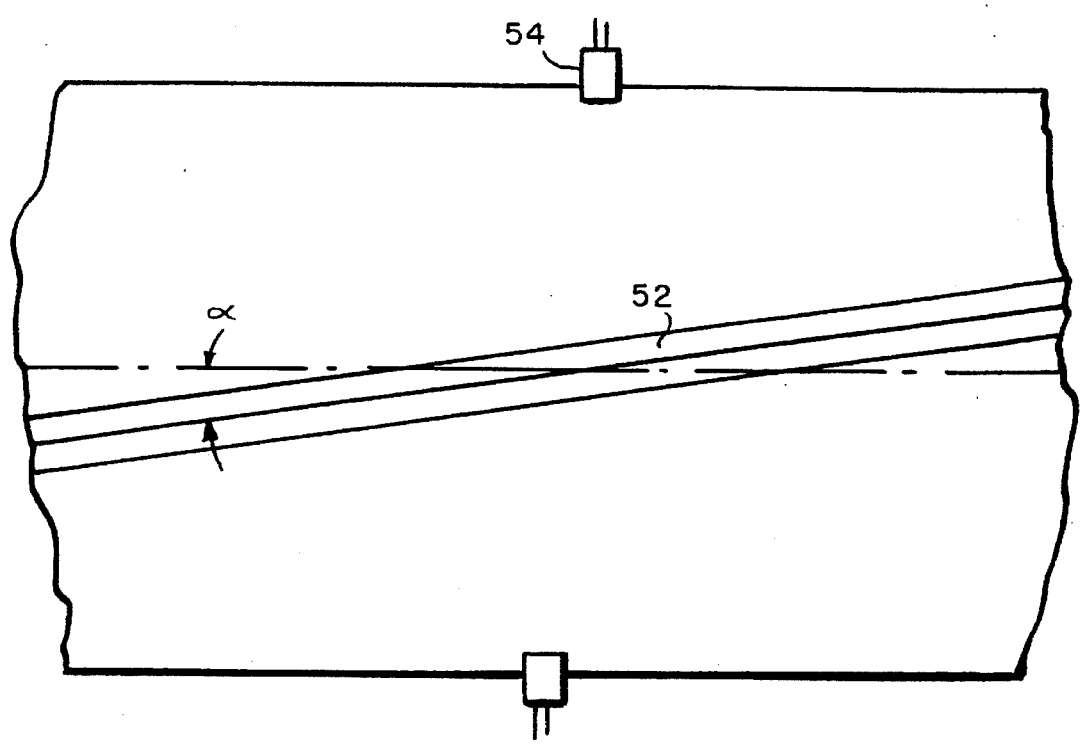
FIG. 5A is a fragmented plan view of the detector showing an X-ray beam penetrating the scintillating screens of FIG. 5.

After exiting the object 32, the collimated pencil-beam is intercepted by a detector 50, illustrated in FIGS. 5 and 5A. Referring to FIG. 5, the detector 50 comprises a plurality of scintillating screens 52 optically coupled to a plurality of photo-multiplier tubes 54 disposed along an inner reflecting surface 55 of the detector. The detector 50 is preferably 4 feet deep, 20 feet long and 2 feet wide. The distance d projected by the scintillating screens is 2 centimeters wide so as to sufficiently encompass the width of the pencil-beam.

The scintillating screen 52 is similar to a conventional screen used in medical applications with film, and is commonly referred to as an "intensifying screen". The X-ray path in the scintillating screen is generally long and may be created by slanting the screen at a small angle with respect to the beam. FIG. 5A shows the beam entering from the left and penetrating two screens 52, each of which have a thickness of 0.5 ram. These screens are relatively opaque to visible light, so the beam must impinge them at a very small angle α, e.g., a 1° angle. Specifically, the scintillating screens 52 are arranged in a back-to-back configuration to increase the efficiency of the detector 50. When the pencil-beam X rays strike the scintillating screen, visible light is produced and detected by the photo-multiplier tubes 54 which, in turn, generate signals used to form the X-ray image.

Broadly stated, the photo-multiplier 54 is a device comprising a vacuum tube and a photosensitive screen for measuring light. In the illustrative embodiment, the photo-multiplier is 5 inches long with a 3 inch diameter screen. Visible light enters the tube and strikes the screen, and is converted to an electron which strikes an anode. There is an array of anodes that effectively multiply electrons such that the gain of the photo-multiplier is, e.g., $10^6$. Preferably, there are 32 photo-multipliers in the detector.

The photo-multipliers 54 are arranged in parallel and supply a net analog signal that is sampled 1,000 times every 0.1 second. This analog signal is digitized and stored in a memory (not shown) for display on a device, such as a computer screen, as a pixel of an image. The actual number of X-ray photons per pixel that enter the object are $10^5$, that is, there are $10^5$ X-ray photons per pixel. The number of photons per pixel that enter the detector after attenuation by the object may be as small as one or two X ray photons per pixel, which the photo-multipliers are sufficiently sensitive to detect.

As noted, the photo-multiplier tubes detect visible radiation that is instantaneously produced when the high-energy X rays strike the scintillating screens in the detector. In addition to these light photons, a plurality of delayed light photons are generated that subsist for a time comparable to the time required for a sweeping line of pencil-beams. This source of noise, called "after-glow", arises because all of the photomultiplier tubes disposed at each level of the screens are excited. After-glow noise cannot be removed and is a limiting factor in conventional pencil-beam detectors.

In accordance with the invention, the after-glow noise may be reduced by "turning-off selected photo-multipliers. Referring again to FIG. 5, as the X-ray pencil beam strikes the scintillating screens 52, those photo-multipliers 54 that are not in the vicinity of the incident X rays are de-activated. De-activation of the tubes may be accomplished by conventional electronic techniques since the location of the incident beam may be measured at the rotating cylindrical collimator 40. It should be noted that the magnitude of after-glow reduction is the ratio of functioning photo-multiplier tubes to the total number of tubes.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A high-energy X-ray inspection system for inspecting the contents of a container, said inspection system comprising:

a pulsed high-energy source for radiating a cone of X rays, said source contained within an enclosure having an integrally-formed precollimator that limits said radiated cone to a fan-beam of X rays; and a rotating cylindrical collimator for converting said fan-beam into a pencil-beam of X rays, said rotating cylindrical collimator having a helical slit extending along an outer surface thereof, said fan-beam intersecting said helical slit along a chord of said outer surface to generate a line of pencil-beams for penetrating the container.

2. The inspection system of claim 1 wherein said high-energy source is a pulsed linear accelerator having a repetition rate of 10,000 pulses per second.

3. The inspection system of claim 2 wherein said precollimator comprising a shield and a slit.

4. The inspection system of claim 3 further comprising a detector for intercepting said pencil-beam penetrating the container and for transforming said line of pencil-beams into image data.

5. The inspection system of claim 4 further comprising a fixed-slit collimator arranged between said rotating cylindrical collimator and the container, said fixed-slit collimator further limiting said line of pencil-beams prior to penetrating the container.

6. The inspection system of claim 5 wherein said detector comprises a plurality of scintillating screens optically coupled to a plurality of photo-multiplier tubes, said scintillating screens being arranged in a back-to-back configuration to increase the efficiency of said detector.

7. A high-energy X-ray inspection system for inspecting the contents of a container, said inspection system comprising:

a pulsed linear accelerator for radiating a cone of X rays, said accelerator contained within an enclosure having an integrally-formed precollimator that limits said radiated cone to a fan-beam of X rays;

a rotating cylindrical collimator for converting said fan-beam into a pencil-beam of X rays, said rotating cylindrical collimator having a helical slit extending along an outer surface thereof, said fan-beam intersecting said helical slit along a chord of said outer surface to generate a sweeping line of pencil-beams for penetrating the container;

a detector for intercepting said sweeping line of pencil-beams penetrating the container and for transforming said sweeping line of pencil-beams into image data; and a fixed-slit collimator situated between said rotating cylindrical collimator and detector, said fixed-slit collimator further limiting said sweeping line of pencil-beams prior to penetrating the container.

8. A method for efficiently inspecting the contents of a container, said method comprising the steps of:

generating a cone of high-energy X rays using a pulsed linear accelerator;

limiting said cone to a fan-beam of X rays with a precollimator;

converting said fan-beam of X rays into a pencil-beam of X rays in response to said fan-beam of X rays intersecting a helical slit of a rotating cylindrical collimator;

collimating said pencil-beam of X rays with a fixed-slit collimator and directing said pencil-beams of X rays through the container;

intercepting said pencil-beams of X rays with a plurality of scintillating screens of a detector and producing visible light in response to said intercepting of said pencil-beams; and activating a selected group of photo-multipliers disposed along said detector to detect the visible light and to produce image data, the activation of said selected group of photo-multipliers reducing noise and improving the quality of said image data.

\* \* \* \* \*